United States Patent [19]
Cheng

[11] Patent Number: 6,099,800
[45] Date of Patent: Aug. 8, 2000

[54] PROCESS FOR CLEANING AND DISINFECTING CONTACT LENS AND HYDROGEN PEROXIDE DESTROYING COMPOSITION HAVING A DELAYED RELEASE FUNCTION FOR USE THEREIN

[75] Inventor: Hui-Wen Cheng, Taipei, Taiwan

[73] Assignee: Sinphar Pharmaceutical Co., Ltd., I-Lan, Taiwan

[21] Appl. No.: 09/134,160

[22] Filed: Aug. 14, 1998

[51] Int. Cl.[7] ....................................................... A61L 12/12
[52] U.S. Cl. ........................................ 422/30; 252/188.21
[58] Field of Search ........................ 422/30; 252/188.21, 252/363.5

[56] References Cited

FOREIGN PATENT DOCUMENTS

86/05695  10/1986  WIPO .
93/04706  3/1993  WIPO .

*Primary Examiner*—Elizabeth McKane
*Attorney, Agent, or Firm*—Bacon & Thomas

[57] ABSTRACT

A hydrogen peroxide destroying composition is disclosed, which includes 1–30% of a hydrogen peroxide destroying component, 0.5–40% of a binder, 0–20% of a disintegrant and 0.02–3% of a chlorophyll coloring agent, based on the weight of the hydrogen peroxide destroying composition. When the hydrogen peroxide destroying composition of the present invention in the form of a tablet or pills added into a $H_2O_2$-containing aqueous medium for disinfecting contact lens, said coloring agent will color the aqueous medium indicating an initiation of neutralization of residual $H_2O_2$ caused by the hydrogen peroxide destroying component after a period of time from the addition.

8 Claims, No Drawings

PROCESS FOR CLEANING AND DISINFECTING CONTACT LENS AND HYDROGEN PEROXIDE DESTROYING COMPOSITION HAVING A DELAYED RELEASE FUNCTION FOR USE THEREIN

FIELD OF THE INVENTION

The present invention is related to a hydrogen peroxide destroying composition having a delayed release function for use in a contact lens one-step cleaning and disinfecting process. In particular, the present invention is related to a hydrogen peroxide destroying composition which has a function of delayed releasing a hydrogen peroxide destroying component contained therein and a function of showing a sign of an initiation of neutralization of residual $H_2O_2$ caused by the hydrogen peroxide destroying component.

BACKGROUND OF THE INVENTION

Contact lenses should be periodically cleaned and disinfected by the user to prevent infection or other deleterious effects on ocular health which may be associated with contact lens wear. Currently, there are several different conventional systems and methods which enable the user to clean and disinfect their contact lenses between wearing times. These conventional cleaning and disinfection systems can be divided into "hot" and "cold" systems. Hot systems require the use of heat to disinfect the contact lenses, whereas cold Systems use chemical disinfectants at ambient temperatures to disinfect the lenses.

Within the realm of cold disinfection systems are hydrogen peroxide disinfection systems. Disinfecting hydrogen peroxide solutions are effective to kill the bacteria and fungi which may contaminate contact lenses, however, residual hydrogen peroxide on a disinfected contact lens may cause irritation, burning or trauma to the eye unless this hydrogen peroxide is destroyed, i.e., decomposed, neutralized, inactivated or chemically reduced. Therefore, the destruction of the residua hydrogen peroxide in the liquid medium containing the disinfected contact lens is needed to enable safe and comfortable wear of the disinfected contact lens.

Contact lenses can be cleaned by enzymatic action. For example, Huth, et al U.S. Pat. No. RE. 32,677 discloses the simultaneous cleaning and disinfecting of contact lenses by a method which comprises contacting the lenses with a solution comprising a disinfecting amount of peroxide and an effective amount of peroxide-active proteolytic enzyme for a time sufficient to remove substantially all protein accretions and to disinfect the lenses. This patent further discloses that catalyze organic enzymes which catalyze the degradation of per-oxides, can be incorporated into tablets and powder, particularly in time-release form both the proteolytic enzyme and the catalyze should have high activity to provide a highly effective degree of cleaning and peroxide degradation, respectively.

Associated with the problem of hydrogen peroxide destruction in contact lens disinfection systems are the problems of easy use and user compliance. To enhance user compliance and ease of use, several efforts have focused on one-step disinfection and hydrogen peroxide destruction. In this regard, various time release tablets containing a core tablet and a totally soluble or insoluble coating have been suggested. Typical examples can be found in U.S. Pat. Nos. 4,568,517; 4,767,559; and 5,145,644.

The tablet having a barrier coating described in the above-mentioned prior art suffers the following disadvantages:

1. A complicated manufacturing process which requires a tableting procedure to form a naked tablet and a coating procedure for forming a barrier layer on the naked tablet;
2. A relatively high manufacturing cost; and
3. The tablet is vulnerable during manufacturing, transportation and storage so that pinholes and/or cracks are formed on the barrier coating, and thus the delayed release function is adversely affected or lost.

The primary objective of the present invention is to provide a hydrogen peroxide destroying composition which does not have the aforesaid drawbacks of the prior art.

A further objective of the present invention is to provide a hydrogen peroxide destroying composition which has a function of delayed releasing a hydrogen peroxide destroying component contained therein and a function of showing a sign of an initiation of neutralization of $H_2O_2$ caused by the hydrogen peroxide destroying component.

SUMMARY OF THE INVENTION

In order to accomplish the above objectives a hydrogen peroxide destroying composition prepared in accordance with the present invention comprises 1–30% of a hydrogen peroxide destroying component, 0.5–40% of a binder, 0–20% of a disintegrant and 0.02–3%, preferably 0.1–2.0%, of a coloring agent, based on the weight of the hydrogen peroxide destroying composition. When the hydrogen peroxide destroying composition of the present invention is added into a $H_2O_2$-containing aqueous medium, said coloring agent will color the aqueous medium indicating an initiation of neutralization of $H_2O_2$ caused by the hydrogen peroxide destroying component after a period of time from the addition.

The present invention also discloses a process for one-step cleaning and disinfecting contact lens comprising placing the contact lens into a $H_2O_2$-containing aqueous medium; and simultaneously adding one or a plurality of tablets or pills into the $H_2O_2$-containing aqueous medium, wherein said tablets or pills have a hydrogen peroxide destroying composition comprising 1–30% of a hydrogen peroxide destroying component, 0.5–40% of a binder, 0–20% of a disintegrant and 0.02–3%, preferably 0.1–2.0%, of a coloring agent, based on the weight of the hydrogen peroxide destroying composition. Preferably, said $H_2O_2$-containing aqueous medium is maintained at a pH value ranging from about 5 to about 9 after the contact lens and the tablets or pills are immersed therein.

The hydrogen peroxide destroying composition of the present invention is preferably in the form of a tablet or pill, which can be formed by a conventional one-step tableting process with a reduced manufacturing cost. Moreover, the risk of losing the delayed release function caused by pin holes and/or cracks on the barrier coating of the conventional hydrogen peroxide destroying composition in the coated tablet form can be avoided in the present invention, because the hydrogen peroxide destroying composition of the present invention in the form of a tablet or pill have a substantially uniform composition and are free of the barrier coating.

DETAILED DESCRIPTION OF THE INVENTION

The present invention discloses a hydrogen peroxide destroying composition having a delayed release function for use simultaneously with a $H_2O_2$-containing aqueous liquid medium to clean and disinfect contact lens at ambient temperatures.

The hydrogen peroxide destroying composition of the present invention comprises 1–30% of a hydrogen peroxide destroying component; 0.5–40%, preferably 1–25%, and more preferably 2.5–10%, of a binder; 0–20%, preferably 0–5%, and more preferably 0–2%, of a disintegrant; and 0.02–3% of a coloring agent, based on the weight of the hydrogen peroxide destroying composition.

Preferably, said coloring agent is chlorophyll.

Said hydrogen peroxide destroying component can be any compounds known in the art which decompose neutralize, inactivated or chemically reduce the hydrogen peroxide, such as enzymes, catalases and reducing agents. Preferably, it is selected from the group consisting essentially of thiosulfates, sulfites, alkali metal salts, thiourea, ascorbic acid, iso-ascorbic acid, N-acetylcysteine, glyoxylic acid, peroxidase, catalase and mixtures thereof. Among them catalase and mixtures containing catalase are the most preferable.

Suitable binders for use in the present invention include any known pharmaceutical binders used in forming a tablet and soluble in water. Typical examples include (but not limited to) polyvinyl acetate, polyvinyl pyrrolidone, polyvinyl alcohol, cellulose ethers, the derivatives thereof, and the mixtures thereof.

The disintegrant of the composition of the present invention can be any known pharmaceutical disintegrants for use in tableting. The content of disintegrant in the composition of the present invention depends on the recipe of the $H_2O_2$-containing aqueous liquid medium, and increases as the $H_2O_2$ concentration of the $H_2O_2$-containing aqueous liquid medium increases. The disintegrant can be omitted from the composition of the present invention, if a long delayed-release function is required due to a low $H_2O_2$ concentration of the $H_2O_2$-containing aqueous liquid medium.

The hydrogen peroxide destroying composition of the present invention is in the form of a tablet or pill, which can be prepared by a conventional one-step tableting process. The tablet or pill should have a hardness greater than about 5 Kg, preferably greater than 8 Kg, and more preferably greater than 10 Kg. Moreover, the brittleness of the tablet or pill should not less than 1%. The hardness of greater than 5 Kg and brittleness greater than 1% are essential for the tablet or pill of the hydrogen peroxide destroying composition of the present invention to have a desired delayed-release function. The tablet or pill form of the present hydrogen peroxide destroying composition have a substantially uniform composition, and will break down and release the hydrogen peroxide destroying component after a period of time starting from the cleaning and the disinfecting process, so that any residual $H_2O_2$ can be destroyed. The coloring agent will also be released at the same time and thus color the $H_2O_2$-containing aqueous liquid medium, indicating an initiation of neutralization of $H_2O_2$ (decomposing of $H_2O_2$) caused by the hydrogen peroxide destroying component.

The $H_2O_2$-containing aqueous liquid medium is available from the market. The amount of $H_2O_2$ contained in the commercially available $H_2O_2$-containing aqueous liquid mediums should be sufficient to reduce at least 90% of microbe within 3 hours, preferably within one hour, and most preferably within 10 minutes starting from the cleaning and disinfecting process. Alternatively, any compounds which can produce $H_2O_2$ in-situ can be used to replace the $H_2O_2$-containing aqueous liquid medium. These compounds, for example sodium peroxide and peracetic acid, can be liquid, powder, or tablet. A contact lens cleaning and disinfecting liquid medium can be prepared with these compounds by diluting or dissolving with water.

The amount of the hydrogen peroxide destroying component contained in the hydrogen peroxide destroying composition ideally is equivalent to a stoichiometric amount for destroying a residual hydrogen peroxide completely in the cleaning and disinfecting process. Taking catalase as an example, 100–250 I.U. catalase per ml of 1 vol % $H_2O_2$ aqueous solution is a suitable concentration for destroying the $H_2O_2$ completely, and 150–200 catalase per ml of 1 vol % $H_2O_2$ aqueous solution is more preferable. Therefore, once the content of the hydrogen peroxide destroying component contained in the hydrogen peroxide destroying composition is fixed, the amount of the hydrogen peroxide destroying composition used is subjected to change by taking the amount of the $H_2O_2$-containing aqueous liquid medium used and its $H_2O_2$ concentration into consideration.

Additionally, any known pharmaceutical diluents and lubricants used in forming a tablet can be incorporated to the hydrogen peroxide destroying composition of the present invention. The amount of the diluent incorporated varies from 10 wt % to 90 wt % based on the weight of the composition and mainly depends on a desired content of the hydrogen peroxide destroying component. Preferably, the amount of the diluent used is 15–60 wt %, and more preferably ranging from 30–50 wt % based on the weight of the composition. The lubricant is used as a fluidizing aid during the tableting.

The hydrogen peroxide destroying composition of the present invention may further comprise cleaning agents for contact lens, wetting/conditioning agents for contact lens, tonicity agents for contact lens, effervescent reagents for contact lens, wetting/conditioning agents for contact lens and a pH buffer. The wetting/conditioning agents for contact lens are able to enhance the wettability and preservability. The tonicity agents for contact lens are able to adjust the osmosis pressure between the contact lens and the eyes.

A typical effervescent reagent for use in the present invention is sodium hydrogen carbonate. The effervescent reagent has a function to accelerate the break down of the hydrogen peroxide destroying tablet or pill of the present invention, and has a function to enhance the cleaning effect. These are because the effervescent reagent produces carbon dioxide while dissolving in the $H_2O_2$-containing liquid medium, creating turbulent flows therein, so that accelerate the mixing of components in the liquid medium, and thus enhance the break down of the tablet and the cleaning of the dirt adhered on the contact lens.

The pH buffer is to adjust the pH value of the final liquid medium after the cleaning and disinfecting process is finished. Any pH buffers able to maintain the final liquid medium at a pH value ranging from 5 to 9 can be used in the present invention such as phosphates and borates, in which the compounds per se having a disinfecting ability are preferable such as borates.

The tablet or pill of the hydrogen peroxide destroying composition of the present invention are designed to break down and release the hydrogen peroxide destroying component at a time when the cleaning and disinfecting process is substantially finished. The cleaning and disinfecting process may take 5 minutes up to 12 hours, generally from 10 to 20 minutes, depending on the $H_2O_2$ concentration of the $H_2O_2$-containing aqueous liquid medium. Accordingly, the tablet or pill of the hydrogen peroxide destroying composition of the present invention will break down and release the hydrogen peroxide destroying component at a time ranging from 5 minutes to 12 hours after the cleaning and disinfecting process is started. Moreover, the tablet or pill of the hydrogen peroxide destroying composition of the present invention are designed to completely decompose the residual hydrogen peroxide within 8 hours, preferably within 2 hours, and more preferably within 30 minutes. These can be done by adjusting the formulation of the hydrogen peroxide destroying composition of the present invention. The content of the binder is decreased and the content of the disintegrant is increased when the tablet or pill of the hydrogen peroxide destroying composition of the present invention require a fast delayed-release, and vise versa. The content of the hydrogen peroxide destroying component is approximately counter-proportional to the time for completely decomposing the residual hydrogen peroxide.

The present The invention will be further illustrated by the following examples. The following examples are only meant to illustrate the invention, but not to limit it.

EXAMPLE 1

A table was formed by using the following formula:

| Catalase | 3500 I.U. |
|---|---|
| Sodium phosphate, tribasic | 1.2 mg |
| Mannitol | 52.0 mg |
| Hydroxylpropylmethyl cellulose (HPMC) | 26.2 mg |
| Polyethylene glycol (PEG 6000) | 20.0 mg |
| Chlorophyll | 0.6 mg. |

To 10 ml of a commercially available $H_2O_2$-containing (3%) contact lens disinfecting liquid medium in a contained the tablet prepared above was added. The $H_2O_2$ concentration of the resulting mixture was measured with a test paper sold under a code of Merckoquant 1.10011.0001 by Merck company (Germany). The results are shown as follows:

| Time (minutes) | $H_2O_2$ Conc. (ppm) |
|---|---|
| 0 | 30000 |
| 15 | 12500 |
| 30 | 5000 |
| 60 | 500 |
| 90 | 2 |
| 120 | 0.2 |
| 240 | 0 |

It can be seen from the above data that the tablet prepared according to The present invention does have a delayed-release function, and the delayed release time is about 4–5 hours.

EXAMPLE 2

Two tablets were prepared and the delayed release function of the tablets were determined by repeating the procedures in Example 1 except that the amount of catalase was replaced by those listed below:

| Catalase, I.U. | Time when $H_2O_2$ Conc. reaches 0 ppm, hours |
|---|---|
| 2000 | 12–16 |
| 3500 | 4–5 |

The data shown above indicate that the $H_2O_2$ concentration of the resulting mixture takes a much shorter time to reach 0 ppm as the content of the catalase in the composition increases.

EXAMPLE 3

A tablet was formed by using the following formula:

| Catalase | 3500 I.U. |
|---|---|
| Hydroxylpropylmethyl cellulose (HPMC) | 33.8 mg |
| Sodium phosphate, tribasic | 1.8 mg |
| Sorbitol | 67.4 mg |
| Polyvinyl pyrrolidone | 6.5 mg |
| Chlorophyll | 0.5 mg. |

The delayed release function of the tablet was determined by repeating the procedures in Example 1. The results shown this tablet has a delayed release time of 10 minutes and the $H_2O_2$ concentration of the resulting mixture reaches 0 within 240 minutes.

What is claimed is:

1. A process for cleaning and disinfecting contact lens comprising immersing the contact lens in a predetermined volume of a $H_2O_2$-containing aqueous medium; and immediately followed by or simultaneously adding one or a plurality of tablets or pills into the $H_2O_2$-containing aqueous medium, wherein said tablets or pills have a hydrogen peroxide destroying composition comprising 1–30% of a hydrogen peroxide destroying component, 0.5–40% of a binder, 0–20% of a disintegrant and 0.02–3% of chlorophyll as a coloring agent, based on the weight of the hydrogen peroxide destroying composition, wherein said chlorophyll coloring agent will color the aqueous medium indicating an initiation of neutralization of residual $H_2O_2$ caused by the hydrogen peroxide destroying component after a period of time from the addition.

2. The process according to claim 1, wherein said hydrogen peroxide destroying component is selected from the group consisting essentially of thiosulfates, sulfites, alkali metal salts, thiourea, ascorbic acid, iso-ascorbic acid, N-acetylcysteine, glyoxylic acid, peroxidase, catalase and mixtures thereof.

3. The process according to claim 2, wherein said hydrogen peroxide destroying component is a catalase or a mixture containing catalase.

4. The process according to claim 1, wherein said $H_2O_2$-containing aqueous medium is maintained at a pH value ranging from about 5 to about 9 after the contact lens and the tablets or pills are immersed therein.

5. A hydrogen peroxide destroying composition comprising 1–30% of a hydrogen peroxide destroying component, 0.5–40% of a binder, 0–20% of a disintegrant and 0.02–3% of chlorophyll as a coloring agent, based on the weight of the hydrogen peroxide destroying composition.

6. The composition according to claim 5, wherein said hydrogen peroxide destroying component is selected from the group consisting essentially of thiosulfates, sulfites, alkali metal salts, thiourea, ascorbic acid, iso-ascorbic acid, N-acetylcysteine, glyoxylic acid, peroxidase, catalase and mixtures thereof.

7. The composition process according to claim 6, wherein said hydrogen peroxide destroying component is a catalase or a mixture containing catalase.

8. The composition according to claim 5, wherein the content of said chlorophyll is 0.1–2.0% based on the weight of the hydrogen peroxide destroying composition.

* * * * *